(12) United States Patent
Nguyen

(10) Patent No.: US 7,351,847 B2
(45) Date of Patent: Apr. 1, 2008

(54) GRIGNARD PROCESSES WITH INCREASED CONTENT OF DIPHENYLCHLOROSILANES

(75) Inventor: Binh Thanh Nguyen, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/585,155

(22) PCT Filed: Dec. 17, 2004

(86) PCT No.: PCT/US2004/043006

§ 371 (c)(1), (2), (4) Date: Jun. 29, 2006

(87) PCT Pub. No.: WO2005/068476

PCT Pub. Date: Jul. 28, 2005

(65) Prior Publication Data

US 2007/0066840 A1    Mar. 22, 2007

Related U.S. Application Data

(60) Provisional application No. 60/534,442, filed on Jan. 6, 2004.

(51) Int. Cl.
C07F 7/04 (2006.01)
C07F 7/08 (2006.01)

(52) U.S. Cl. .......................... 556/480; 546/14
(58) Field of Classification Search ................ 556/480; 546/14

See application file for complete search history.

(56) References Cited

U.S. PATENT DOCUMENTS

| | | | |
|---|---|---|---|
| 2,426,122 A | 8/1947 | Rust et al. | |
| 2,795,627 A | 6/1957 | Ramsden et al. | |
| 2,795,628 A | 6/1957 | Ramsden et al. | |
| 2,816,937 A | 12/1957 | Ramsden et al. | |
| 2,894,012 A | 7/1959 | Ramsden et al. | |
| 3,095,460 A | 6/1963 | Olah et al. | |
| 3,140,321 A | 7/1964 | Goepfert et al. | |
| 3,264,360 A | 8/1966 | Nudenberg et al. | |
| 3,485,863 A | 12/1969 | Nutzel et al. | |
| 4,127,507 A | 11/1978 | Fannin et al. | |
| 4,593,112 A | 6/1986 | Takamizawa et al. | |
| 4,687,874 A | 8/1987 | Oswald et al. | |
| 4,921,989 A | 5/1990 | Ishihara et al. | |
| 5,099,040 A | 3/1992 | Rosen et al. | |
| 5,242,625 A | 9/1993 | Jones et al. | |
| 5,596,120 A | 1/1997 | Bank et al. | |
| 5,606,088 A | 2/1997 | Bank et al. | |
| 5,629,439 A | 5/1997 | Bank et al. | |
| 6,057,480 A | 5/2000 | Ueno et al. | |
| 6,541,651 B1* | 4/2003 | Bedbury et al. | ............ 556/480 |
| 6,552,237 B1* | 4/2003 | Bedbury et al. | ......... 568/909.5 |
| 6,686,492 B2* | 2/2004 | Nguyen | ....................... 556/480 |
| 7,084,206 B2* | 8/2006 | Bedbury et al. | ............ 524/858 |
| 2003/0191238 A1 | 10/2003 | Bedbury et al. | |
| 2005/0068475 A1 | 3/2005 | Kume et al. | |
| 2005/0068476 A1 | 3/2005 | Okabe | |

FOREIGN PATENT DOCUMENTS

| | | | |
|---|---|---|---|
| DE | 243028 | | 2/1987 |
| DE | 243031 | | 2/1987 |
| EP | 0825195 | | 2/1998 |
| EP | 0729931 | | 8/1998 |
| GB | 622970 | * | 1/1947 |
| GB | 622970 | * | 5/1949 |
| GB | 657704 | | 9/1951 |
| GB | 1120150 | | 7/1968 |
| JP | 62-022790 | | 1/1987 |
| JP | 03-109389 | | 5/1991 |
| JP | 08-245641 | | 9/1996 |
| JP | 08333374 | | 12/1996 |
| RU | 2174124 | | 9/2001 |
| SU | 477626 | | 8/1985 |
| WO | WO 03/084901 | | 10/2003 |
| WO | WO 03/084967 | | 10/2003 |
| WO | WO 03/084970 | | 10/2003 |
| WO | WO 03/106465 | | 12/2003 |
| WO | WO 2005/068475 | | 7/2005 |
| WO | WO 2005/068476 | | 7/2005 |
| WO | WO 2006/083665 | | 8/2006 |

OTHER PUBLICATIONS

Emeleus et al., Journal of the Chemical Society (1947), 1592-1594.*
Lennon, Patrick J. et al: "Nuclephilic catalysis of organosilicon substitution reactions" Organometallics, 8(4), 1121-2 Coden: ORGND7; ISSN: 0276-7333, 1989, XP002322018.

(Continued)

Primary Examiner—Yvonne (Bonnie) Eyler
Assistant Examiner—Chukwuma O. Nwaonicha
(74) Attorney, Agent, or Firm—Patricia M. Scaduto

(57) ABSTRACT

Three improved Grignard processes are used for preparing phenyl-containing chlorosilane products wherein the yield of diphenylchlorosilanes as a product is maximized, while the yield of phenylchlorosilanes as a product is minimized. In one embodiment, the process involves contacting a phenyl Grignard reagent, an ether solvent, an aromatic halogenated coupling solvent and a trichlorosilane. In another embodiment, the process involves contacting a phenyl Grignard reagent, an ether solvent, an aromatic halogenated coupling solvent, a trichlorosilane, and a phenylchlorosilane. In yet another embodiment, the process involves contacting a phenyl Grignard reagent, an ether solvent, an aromatic halogenated coupling solvent, and a phenylchlorosilane. In each embodiment, the reactants are present in particular mole ratios of the components.

16 Claims, No Drawings

OTHER PUBLICATIONS

Semenov V. V. et al., Reactions of Methylchlorodisilanes with Grignard Reagents, Russian Chemical Bulletin, vol. 44, No. 5, 1995, pp. 927-930.

Kunai, A. et al.: "Highly selective synthesis of chlorosilanes from hydrosilanes", ORGANOMETALLICS, 11(7), pp. 2708-2711, 1992, XP009068024.

Hyde, J. F. et al: "Condensation products of the organo-silane diols", Journal of the American Chemical Society, 63(5), May 1941, pp. 1194-1196, XP009068013.

Tuulmets, et al., Partially Solanted Alkylmagnesium Chlorides in Toluene, Jur. Of Organometallic Chem., vol. 523, Oct. 18, 1996, pp. 133-138.

Tuulmets, et al., Solvation Effects in Partially Solvated Grignard Reagents, Jour. Of Organometallic Chem., vol. 575 (1999) pp. 182-186.

Coates et al., Organomethallic Compounds, vol. 1, pp. 76-103, 1967, Methuen and Co. Ltd, London, U.K.

Kirk/Orthmer, Encylopedia of Chemical Technology, vol. 10, 721-734 (1966) The interscience Enclyopedia, Inc., NY NY.

Turk, et al., Organic Systhesis, vol. 27, 7-8 (1947).

Tuulmets A. et al., Gringnard Reagents in Toulene Solutions, Applied Organometallic Chemistry, vol. 16, Jul. 23, 2002, pp. 525-529.

Tuulmets A. et al., Reactions of partially solvated Grignard reagents with a ketone, Journal of Organometallic Chemistry Elsevier-Sequoia S.A. Lausanne, CH, vol. 586, No. 2, Sep. 5, 1999 pp. 145-149.

Tuulmets A. et al., Influence of sonication of Grignard reagent formation, Ultrasonics: Sonochemistry, Butterworth-Heinemann, GB, vol. 2, No. 2, Oct. 1, 1995, pp. S75-S78.

Kolodyazhnyi Y. V. et al., Structure and Donor Activity in Organometallic Compounds, Jouranl of General Chemistry of the USSR, vol. 52, No. 3, 1982, pp. 554-558.

* cited by examiner

GRIGNARD PROCESSES WITH INCREASED CONTENT OF DIPHENYLCHLOROSILANES

CROSS REFERENCE TO RELATED APPLICATIONS

This application is a U.S. national stage filing under 35 U.S.C. §371 of PCT Application No. PCT/US04/043006 filed on 17 Dec. 2004, currently pending, which claims the benefit of U.S. Provisional Patent Application No. 60/534,442 filed 06 Jan. 2004 under 35 U.S.C. §119(e). PCT Application No. PCT/US04/043006 and U.S. Provisional Patent Application No. 60/534,442 are hereby incorporated by reference.

DESCRIPTION

This invention is related to Grignard processes for preparing phenyl-containing chlorosilane products. In particular, it relates to Grignard processes in which the yield of diphenylchlorosilanes as a product is maximized, and the yield of phenylchlorosilanes as a product is minimized.

In copending U.S. patent application Ser. No. 10/117,259, filed on Apr. 4, 2002, entitled "Process for Preparing Phenylorganosilicon Intermediates" (the '259 application hereafter), assigned to the same assignee as the present invention, a Grignard process is described in which the yield of phenylchlorosilanes as a product is maximized and the yield of diphenylchlorosilanes as a product is minimized. In fact, the diphenylchlorosilanes prepared in the '651 patent are only present as by-products.

This invention in contrast, is characterized in that it seeks to obtain an opposite result, i.e., to minimize the yield of phenylchlorosilanes as a product while maximizing the yield of diphenylchlorosilanes as a product. Achievement of this goal is obtained by carrying out the Grignard process using certain mole ratios of the reactants used in the Grignard process.

This invention is directed to three improved Grignard processes for preparing phenyl-containing chlorosilane products in which the yield of diphenylchlorosilanes as a product is maximized, and the yield of phenylchlorosilanes as a product is minimized.

In a first normal coupling process embodiment, the process involves contacting a phenyl Grignard reagent, an ether solvent, an aromatic halogenated coupling solvent, and a trichlorosilane, in a mole ratio of 1/4/3/0.5, respectively.

In a second co-coupling process embodiment, the process involves contacting a phenyl Grignard reagent, an ether solvent, an aromatic halogenated coupling solvent, a trichlorosilane, and a phenylchlorosilane, in a mole ratio of 1/4/3/1.3/0.38, respectively.

In a third direct coupling process embodiment, the process involves contacting a phenyl Grignard reagent, an ether solvent, an aromatic halogenated coupling solvent, and a phenylchlorosilane, in a mole ratio of 1/4/3/1.1, respectively.

In the first embodiment, the mole ratio of the ether solvent to the phenyl Grignard reagent is 2 to 5, the mole ratio of the aromatic halogenated coupling solvent to the phenyl Grignard reagent is 3 to 7, and the mole ratio of the trichlorosilane to the phenyl Grignard reagent is 0.1 to 10. In the second embodiment, the mole ratio of the ether solvent to the phenyl Grignard reagent is 2 to 5, the mole ratio of the aromatic halogenated coupling solvent to the phenyl Grignard reagent is 3 to 7, the mole ratio of the trichlorosilane to the phenyl Grignard reagent is 0.1 to 10, and the mole ratio of the phenylchlorosilane to the phenyl Grignard reagent is 0.5 to 5. In the third embodiment, the mole ratio of the ether solvent to the phenyl Grignard reagent is 2 to 5, the mole ratio of the aromatic halogenated coupling solvent to the phenyl Grignard reagent is 3 to 7, and the mole ratio of the phenylchlorosilane to the phenyl Grignard reagent is 0.5 to 5.

These and other features of the invention will become apparent from a consideration of the detailed description.

As used herein, the term normal coupling refers to reactions of a phenyl Grignard reagent chloride with a trichlorosilane; the term co-coupling refers to reactions of the phenyl Grignard reagent the trichlorosilane and a phenylchlorosilane; and the term direct coupling refers to reactions of the phenyl Grignard reagent with the phenylchlorosilane The Grignard process according to this invention is illustrated below in chemical reactions (I) and (II). Chemical reaction (II) depicts the first embodiment of the invention (normal coupling). Chlorobenzene is also one of the products in chemical reaction (II) but is not shown in chemical reaction (II).

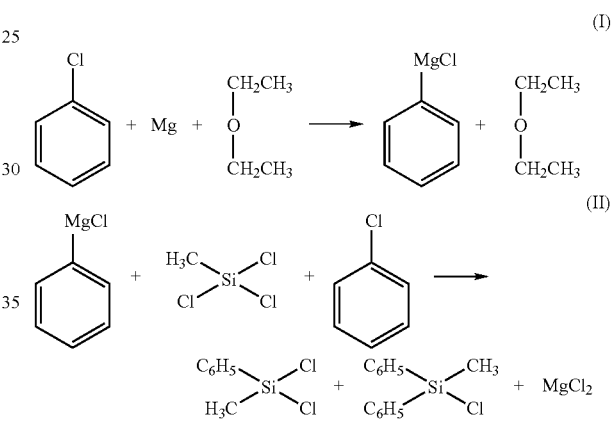

In chemical reaction (I), phenyl chloride/chlorobenzene (PhCl) is combined with magnesium metal (Mg) in the presence of the solvent diethyl ether ($CH_3CH_2$—O—$CH_2CH_3$), to form phenyl magnesium chloride (PhMgCl) in diethyl ether. Phenyl magnesium chloride in diethyl ether is then used in chemical reaction (II) where it is combined with methyltrichlorosilane ($MeSiCl_3$) and the coupling solvent chlorobenzene. The products of chemical reaction (II) are phenylmethyldichlorosilane ($PhMeSiCl_2$), diphenylmethylchlorosilane ($Ph_2MeSiCl$), magnesium chloride, and chlorobenzene.

According to the second embodiment of the invention (co-coupling) depicted below as chemical reaction (III), phenylmethyldichlorosilane is added as an additional reactant along with methyltrichlorsilane. Chorobenzene is also one of the products in chemical reaction (III) but is not shown in chemical reaction (III).

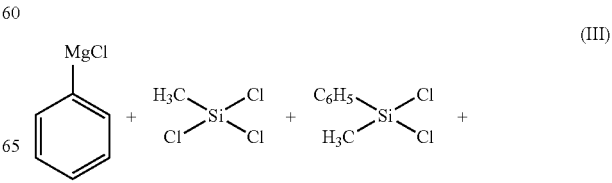

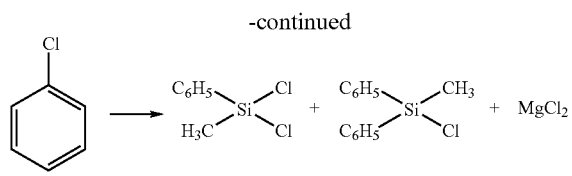

The third embodiment of the invention (direct coupling) is similar to the first embodiment of chemical reaction (II), except that in the third embodiment in chemical reaction (IV), phenylmethyldichlorosilane is used instead of methyltrichlorosilane. Chorobenzene is also one of the products in chemical reaction (IV) but is not shown in chemical reaction (IV).

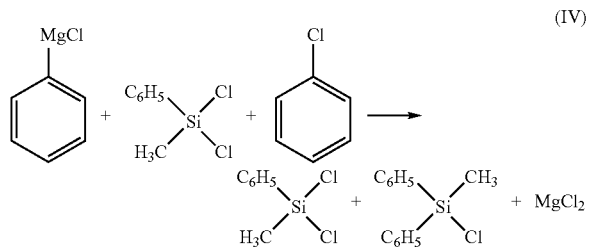

In the first embodiment of this invention (normal coupling), the mole ratio of PhMgCl/ether/chlorobenzene/MeSiCl$_3$ is 1/4/3/0.5, respectively, as compared to the corresponding mole ratio of PhMgCl/ether/chlorobenzene/MeSiCl$_3$ in the '259 application of 1/0.08/4/2, in Example 3.

In the second embodiment of this invention (co-coupling), the mole ratio of PhMgCl/ether/chlorobenzene/MeSiCl$_3$/PhMeSiCl$_2$ is 1/4/3/1.3/0.38, respectively. This co-coupling method, however, is not even disclosed in the '259 application.

In the third embodiment of this invention (direct coupling), the mole ratio of PhMgCl/ether/chlorobenzene//PhMeSiCl$_2$ is 1/4/3/1.1, respectively. This direct coupling method, however, is not even disclosed in the '259 application.

It should be noted that there are significant differences between the three processes described in this invention in comparison to the single process described in the common assignee's '259 application. Thus, the mole ratio according to the first embodiment of this invention (normal coupling) is different than the mole ratio in the '259 application, and this results in an almost three-fold increase in the yield of diphenylmethylchlorosilane in comparison to the yield of only about 6 percent obtained in the '259 application. In addition, neither of the processes of the second embodiment (co-coupling) and of the third embodiments (direct coupling) are even present in the '259 application.

These differences are also significant in that the thrust and focus of the '259 application is the production of phenylmethyldichlorosilane as the primary and major product of the reaction, whereas the thrust and focus of the present invention is the production of diphenylmethylchlorosilane as the desirable product of the three processes. Thus, by following the teaching of the method according to the first embodiment of this invention, it is possible for one skilled in the art to prepare products of the process containing about 20 percent or more by weight of diphenylmethylchlorosilane, as compared to the products obtained in the '259 application which contain only about 1-6 percent by weight of phenylmethyldichlorosilane. The '259 application is completely silent regarding the second and third process embodiments of this invention.

Chlorosilanes useful according to the invention have the general formula R$_a$SiX$_{4-a}$ wherein each R can represent a phenyl group, methyl group, vinyl group, or hydrogen; X represents chlorine or bromine; and $a$ has a value of 0, 1, or 2. Some suitable and representative chlorosilanes which can be used include silicon tetrachloride, methyltrichlorosilane, dimethyldichlorosilane, phenylmethyldichlorosilane, phenyltrichlorosilane, diphenyldichlorosilane, vinyltrichlorosilane, hydridotrichlorosilane, divinyldichlorosilane, methylvinyldichlorosilane, phenylvinyldichlorosilane, hydridomethyldichlorosilane, hydridophenyldichlorosilane, hydridovinyldichlorosilane and dihydridodichlorosilane.

Magnesium metal useful in this invention can be any of the forms of the metal currently being used in Grignard-type reactions. For example, the metal can be in the form of a powder, flake, granule, chip, lump, or shaving. Contact of the magnesium metal with the phenyl halide can be undertaken in standard type reactors suitable for running Grignard type reactions. Thus, the reactor can be a batch, semi-batch, or continuous type reactor. A preferred reactor is a continuous reactor. The environment in which the present method is carried out should be inert for best results. Therefore, under preferred conditions of the method, the reactor is purged and blanketed with an inert gas such as nitrogen or argon.

Phenyl halides useful in this invention are those of the formula RX wherein R represents phenyl and X is a chlorine or bromine atom. The preferred phenyl halide for this invention is phenyl chloride (chlorobenzene). Solvents for synthesizing the Grignard reagent include dialkyl ethers such as dimethyl ether, diethyl ether, ethylmethyl ether, n-butylmethyl ether, n-butylethyl ether, di-n-butyl ether, di-isobutyl ether, isobutylmethyl ether, and isobutylethyl ether. The most preferred ether solvent is diethyl ether. Aromatic halogenated solvents such as chlorobenzene and 1,4-dichlorobenzene are used as the coupling solvent in the coupling reaction of the phenyl Grignard reagent PhMgCl with MeSiCl$_3$, mixtures of MeSiCl$_3$ and PhMeSiCl$_2$, or PhMeSiCl$_2$, according to the processes of the invention. Phenyl Grignard reagents such as PhMgCl can either be synthesized or purchased commercially, as desired.

EXAMPLES

The following examples are set forth in order to illustrate the invention in more detail.

Example 1

Normal Coupling Method

In this example, the coupling mole ratio was 1/4/3/0.5 of phenylmagnesium chloride/diethyl ether/chlorobenzene/methyltrichlorosilane (PhMgCl/Et$_2$O/C$_6$H$_5$Cl/MeSiCl$_3$). The MeSiCl$_3$ and the Grignard solution (PhMgCl/Et$_2$O) used in this example were compositions prepared by an in-house facility. The mole ratio of the Grignard solution was 1/4 PhMgCl/Et$_2$O with a PhMgCl concentration of 2 mol/L. This Grignard solution contained two phases, a liquid phase and a solids phase that settled at the bottom. Both the liquid phase and the solid phase were used in this example. Approximately 250 milliliter of the Grignard solution were transferred to a 500 milliliter addition funnel by means of a pump. The amount of Grignard solution used was the equivalent of about 0.500 mol of PhMgCl and 2.000 mol of Et$_2$O. Then, 37.37 gram (0.25 mol) of MeSiCl$_3$ and 168.75 gram (1.499 mol) of PhCl were added to a 1000 milliliter round bottom flask.

The addition funnel was connected to a source of nitrogen to provide an inert atmosphere for the system and placed on a 500 milliliter three-neck round bottom flask containing a magnetic stirrer. The 500 milliliter three-neck round bottom was charged with the Grignard solution and stirred. From the 500 milliliter three-neck round bottom flask, the Grignard solution was pumped into a reactor. Addition of the Grignard solution took place over a time period of about ten minutes. The solution turned dark orange brown in color but remained in a flowable state throughout the procedure. The maximum exothermic temperature reached was 64° C. When the agitation was stopped, the settling of solids began almost immediately. The reaction mixture was allowed to cool and then it was transferred to a labeled sample jar. The percent mass recovery was determined to be about 94.90 percent.

Gas Chromatography (GC) analysis of the reaction mixture showed that it contained about 20.8 weight percent of the desired component Ph$_2$MeSiCl, and only a small amount, i.e., 0.07 weight percent, of PhMeSiCl$_2$ as a by-product.

Example 2

Co-Coupling Method

In this example, the coupling mole ratio was 1/4/3/1.3/0.38 of phenylmagnesium chloride/diethyl ether/chlorobenzene/methyltrichlorosilane/phenylmethyldichlorosilane (PhMgCl/Et$_2$O/C$_6$H$_5$Cl/MeSiCl$_3$/PhMeSiCl$_2$). The MeSiCl$_3$ and the Grignard solution (PhMgCl/Et$_2$O) used in this example were compositions prepared by an in-house facility. The mole ratio of the Grignard solution was 1/4 PhMgCl/Et$_2$O with a PhMgCl concentration of 2 mol/L. This Grignard solution contained two phases, a liquid phase and a solids phase that settled at the bottom. Both the liquid phase and the solid phase were used in this example. Approximately 250 milliliter of the Grignard solution were transferred to a 500 milliliter addition funnel by means of a pump. The amount of Grignard solution used was the equivalent of about 0.500 mol of PhMgCl and 2.000 mol of Et$_2$O. Then, 99.41 gram (0.67 mol) of MeSiCl$_3$, 36.32 gram (0.19 mol) of PhMeSiCl$_2$, and 168.75 gram (1.499 mol) of PhCl were added to a 1000 milliliter round bottom flask.

The addition funnel was connected to a source of nitrogen to provide an inert atmosphere for the system and placed on a 500 milliliter three-neck round bottom flask containing a magnetic stirrer. The 500 milliliter three-neck round bottom was charged with the Grignard solution and stirred. From the 500 milliliter three-neck round bottom flask, the Grignard solution was pumped into a reactor. Addition of the Grignard solution took place over a time period of about ten minutes. The solution turned dark orange brown in color but remained in a flowable state throughout the procedure. The maximum exothermic temperature reached was 67° C. When the agitation was stopped, the settling of solids began almost immediately. The reaction mixture was allowed to cool and then it was transferred to a labeled sample jar. The percent mass recovery was determined to be about 94.11 percent.

Gas Chromatography (GC) analysis of the reaction mixture showed that it contained about 2.9 weight percent of the desired component Ph$_2$MeSiCl, and about 29.7 weight percent of PhMeSiCl$_2$. In this co-coupling method, the weight ratio of PhMeSiCl$_2$/Ph$_2$MeSiCl was 0.1.

Example 3

Direct Coupling Method

In this example, the coupling mole ratio was 1/4/3/1.1 of phenylmagnesium chloride/diethyl ether/chlorobenzene/phenylmethyldichlorosilane (PhMgCl/Et$_2$O/C$_6$H$_5$Cl/PhMeSiCl$_2$). The MeSiCl$_3$ and the Grignard solution (PhMgCl/Et$_2$O) used in this example were compositions prepared by an in-house facility. The mole ratio of the Grignard solution was 1/4 PhMgCl/Et$_2$O with a PhMgCl concentration of 2 mol/L. This Grignard solution contained two phases, a liquid phase and a solids phase that settled at the bottom. Both the liquid phase and the solid phase were used in this example. Approximately 250 milliliter of the Grignard solution were transferred to a 500 milliliter addition funnel by means of a pump. The amount of Grignard solution used was the equivalent of about 0.500 mol of PhMgCl and 2.000 mol of Et$_2$O. Then, 105.127 gram (0.55 mol) of PhMeSiCl$_2$ and 168.75 gram (1.499 mol) of PhCl were added to a 1000 milliliter round bottom flask.

The addition funnel was connected to a source of nitrogen to provide an inert atmosphere for the system and placed on a 500 milliliter three-neck round bottom flask containing a magnetic stirrer. The 500 milliliter three-neck round bottom was charged with the Grignard solution and stirred. From the 500 milliliter three-neck round bottom flask, the Grignard solution was pumped into a reactor. Addition of the Grignard solution took place over a time period of about 10.5 minutes. The solution turned dark orange brown in color but remained in a flowable state throughout the procedure. The maximum exothermic temperature reached was 62° C. When the agitation was stopped, the settling of solids began almost immediately. The reaction mixture was allowed to cool and then it was transferred to a labeled sample jar. The percent mass recovery was determined to be about 92.11 percent.

Gas Chromatography (GC) analysis of the reaction mixture showed that it contained about 12.18 weight percent of the desired component Ph$_2$MeSiCl, and about 3.6 weight percent of PhMeSiCl$_2$. In this direct coupling method, the weight ratio of PhMeSiCl$_2$/Ph$_2$MeSiCl was 3.4.

Those skilled in the art are cognizant of the fact that it is both difficult and not easily obtainable, to increase the formation of Ph$_2$MeSiCl by a normal coupling reaction of PhMgCl with MeSiCl$_3$, or by a co-coupling reaction of PhMgCl with MeSiCl$_3$ and PhMeSiCl$_2$, or by a direct coupling reaction of PhMgCl with PhMeSiCl$_2$. Contrary to the art however, it has been unexpectedly discovered according to this invention, that by changing the ratio of PhMgCl/MeSiCl$_3$ (normal-coupling), or PhMgCl/MeSiCl$_3$/PhMeSiCl$_2$ (co-coupling), or PhMgCl/PhMeSiCl$_2$ (direct coupling), it is possible to not only improve, but to actually increase the production of Ph$_2$MeSiCl. This is significant, since it now enables those skilled in the art to increase and maximize production of Ph$_2$MeSiCl, while at the same time minimizing production of PhMeSiCl$_2$, by a process not heretofore known.

Other variations may be made in compounds, compositions, and methods described herein without departing from the essential features of the invention. The embodiments of the invention specifically illustrated herein are exemplary only and not intended as limitations on their scope except as defined in the appended claims.

The invention claimed is:

1. A process for preparing diphenylchlorosilanes by the Grignard process comprising contacting a phenyl Grignard reagent, an ether solvent, an aromatic halogenated coupling solvent, and a trichlorosilane; wherein the mole ratio of the phenyl Grignard reagent/ether solvent/aromatic halogenated coupling solvent/trichlorosilane is 1/4/3/0.5.

2. The process according to claim 1 wherein the phenyl Grignard reagent is phenyl magnesium chloride.

3. The process according to claim 1 wherein the ether solvent is a dialkyl ether selected from the group consisting of dimethyl ether, diethyl ether, ethylmethyl ether, n-butylmethyl ether, n-butylethyl ether, di-n-butyl ether, di-isobutyl ether, isobutylmethyl ether, and isobutylethyl ether.

4. The process according to claim 1 wherein the aromatic halogenated coupling solvent is chlorobenzene.

5. The process according to claim 1 wherein the trichlorosilane is selected from the group consisting of methyltrichlorosilane, phenyltrichlorosilane, and vinyltrichlorosilane.

6. A process for preparing diphenylchlorosilanes by the Grignard process comprising contacting a phenyl Grignard reagent, an ether solvent, an aromatic halogenated coupling solvent, a trichlorosilane, and a phenylchlorosilane; wherein the mole ratio of the ether solvent to the phenyl Grignard reagent is 2 to 5, the mole ratio of the aromatic halogenated coupling solvent to the phenyl Grignard reagent is 3 to 7, the mole ratio of the trichlorosilane to the phenyl Grignard reagent is 0.1 to 10, and the mole ratio of the phenylchlorosilane to the phenyl Grignard reagent is 0.5 to 5.

7. The process according to claim 6 wherein the phenyl Grignard reagent is phenyl magnesium chloride.

8. The process according to claim 6 wherein the ether solvent is a dialkyl ether selected from the group consisting of dimethyl ether, diethyl ether, ethylmethyl ether, n-butylmethyl ether, n-butylmethyl ether, di-n-butyl ether, di-isobutyl ether, isobutylmethyl ether, and isobutylethyl ether.

9. The process according to claim 6 wherein the aromatic halogenated coupling solvent is chlorobenzene.

10. The process according to claim 6 wherein the trichlorosilane is selected from the group consisting of methyltrichlorosilane, phenyltrichlorosilane, and vinyltrichlorosilane.

11. The process according to claim 6 wherein the phenylchlorosilane is selected from the group consisting of phenylmethyldichlorosilane, phenyltrichlorosilane, diphenyldichlorosilane, phenylvinyldichlorosilane, and hydridophenyldichlorosilane.

12. A process for preparing diphenylchlorosilanes by the Grignard process comprising contacting a phenyl Grignard reagent, an ether solvent, an aromatic halogenated coupling solvent and a phenylchlorosilane; wherein the mole ratio of the ether solvent to the phenyl Grignard reagent is 2 to 5, the mole ratio of the aromatic halogenated coupling solvent to the phenyl Grignard reagent is 3 to 7, and the mole ratio of the phenylchlorosilane to the phenyl Grignard reagent is 0.5 to 5.

13. The process according to claim 12 wherein the phenyl Grignard reagent is phenyl magnesium chloride.

14. The process according to claim 12 wherein the ether solvent is a dialkyl ether selected from the group consisting of dimethyl ether, diethyl ether, ethylmethyl ether, n-butylnethyl ether, n-butylethyl ether, di-n-butyl ether, di-isobutyl ether, isobutylmethyl ether, and isobutylethyl ether.

15. The process according to claim 12 wherein the aromatic halogenated coupling solvent is chlorobenzene.

16. The process according to claim 12 wherein the phenylchlorosilane is selected from the group consisting of phenylmethyldichlorosilane, phenyltrichlorosilane, diphenyldichlorosilane, phenylvinyldichlorosilane, and hydridophenyldichlorosilane.

* * * * *